US010400275B2

(12) United States Patent
Aurich-Costa

(10) Patent No.: US 10,400,275 B2
(45) Date of Patent: Sep. 3, 2019

(54) METHODS AND KITS FOR ROOM TEMPERATURE IN SITU DETECTION OF A TARGET NUCLEIC ACID IN A BIOLOGICAL SAMPLE

(71) Applicant: Cellay, Inc., Cambridge, MA (US)

(72) Inventor: Joan Aurich-Costa, Cambridge, MA (US)

(73) Assignee: Cellay, Inc., Cambridge, MA (US)

( * ) Notice: Subject to any disclaimer, the term of this patent is extended or adjusted under 35 U.S.C. 154(b) by 368 days.

(21) Appl. No.: 14/844,823

(22) Filed: Sep. 3, 2015

(65) Prior Publication Data

US 2015/0368701 A1 Dec. 24, 2015

Related U.S. Application Data

(62) Division of application No. 13/712,334, filed on Dec. 12, 2012, now Pat. No. 9,145,584.

(60) Provisional application No. 61/569,656, filed on Dec. 12, 2011.

(51) Int. Cl.
*C12Q 1/68* (2018.01)
*C12Q 1/6841* (2018.01)

(52) U.S. Cl.
CPC .................. *C12Q 1/6841* (2013.01)

(58) Field of Classification Search
None
See application file for complete search history.

(56) References Cited

U.S. PATENT DOCUMENTS

| | | | | |
|---|---|---|---|---|
| 5,753,433 A * | 5/1998 | Kessler | ................ | C12Q 1/6855 435/174 |
| 5,753,437 A | 5/1998 | Steeg et al. | | |
| 6,780,603 B1 | 8/2004 | Tsilibary et al. | | |
| 9,145,584 B2 | 9/2015 | Aurich-Costa | | |
| 2002/0155612 A1 | 10/2002 | Bedzyk et al. | | |
| 2002/0197656 A1 | 12/2002 | Li | | |
| 2004/0158883 A1 | 8/2004 | Crawford et al. | | |
| 2007/0128646 A1 | 6/2007 | Fiandaca et al. | | |
| 2009/0036664 A1 | 2/2009 | Peter | | |
| 2010/0285601 A1* | 11/2010 | Kong | ............... | G01N 33/54306 436/94 |
| 2013/0149705 A1 | 6/2013 | Aurich-Costa | | |
| 2013/0203055 A1 | 8/2013 | Aurich-Costa | | |

FOREIGN PATENT DOCUMENTS

| | | |
|---|---|---|
| CN | 101363048 A | 2/2009 |
| CN | 101970451 A | 2/2011 |
| WO | WO 2005/007872 A2 | 1/2005 |
| WO | WO 2005/010203 A2 | 2/2005 |
| WO | WO 2006/108627 A1 | 10/2006 |
| WO | WO 2009/015359 A2 | 1/2009 |
| WO | WO 2011/153354 A1 | 12/2011 |
| WO | WO 2013/090386 A2 | 6/2013 |

OTHER PUBLICATIONS

"RNA hydrolysis" from Wikipedia, the free encyclopedia. Printed on Oct. 26, 2017.*
"What Are the Effects of an Alkaline pH on the Structure of DNA?" from Sciencing.com. Printed on Oct. 26, 2017.*
Ageno et al., The Alkaline Denaturation of DNA. Biophys. J., 9, 1281-1311, 1969.*
"Room temperature" from Wikipedia, the free encyclopedia.Printed on Oct. 26, 2017.*
Final Office Action for U.S. Appl. No. 13/701,310, "Methods and Kits for In Situ Detection of Nucleotide Sequences", dated Sep. 9, 2015.
Communication pursuant to Rule 164(2)(b) and Article 94(3) for EP Application No. 12 806 823.6, "Methods and Kits for Room Temperature In Situ Detection of a Target Nucleic Acid in a Biological Sample", dated Dec. 8, 2015.
Fernández, J.L. and Gosálvez, J., "Application of FISH to Detect DNA Damage. DNA Breakage Detection-FISH (DBD-FISH)." In In Situ *Detection of DNA Damage. Methods and Protocols*, V.V. Didenko eds. (TX: Baylor College of Medicine), pp. 203-216 (2002).
Rivero, M.T., et al., "High Frequency of Constitutive Alkali-Labile Sites in Mouse Major Satellite DNA, Detected by DNA Breakage Detection-Fluorescence In Situ Hybridization", *Mutations Research*, 483:43-50 (2001).
Szigeti, C., et al.,"Comparison of Treatment Regimens to Sensitize In Situ Hybridization for Low-Abundance Calmodulin Transcripts in the White Matter of the Rat Spinal Cord", *Acta Biologica Szegediensis*, 47(1-4_:1-6 (2003).
Notification of Transmittal of the International Search Report and the Written Opinion of the International Searching Authority, or the Declaration, Application No. PCT/US2011/038934, titled "Methods and Kits for In Situ Detection of Nucleotide Sequences", dated Sep. 27, 2011, consisting of 13 pages.
Notification Concerning Transmittal of International Preliminary Report on Patentability for Application No. PCT/US2011/038934, titled "Methods and Kits for In Situ Detection of Nucleotide Sequences", dated Dec. 13, 2012, consisting of 7 pages.
International Preliminary Report on Patentability, for Application No. PCT/US2012/069178, dated Jun. 17, 2014, entitled "Methods and Kits for Room Temperature In Situ Detection of a Target Nucleic Acid in a Biological Sample," consisting of 13 pages.
International Search Report, for Application No. PCT/US2012/069178, entitled "Methods and Kits for Room Temperature In Situ Detection of a Target Nucleic Acid in a Biological Sample", dated Nov. 7, 2013.

(Continued)

*Primary Examiner* — Frank W Lu

(74) *Attorney, Agent, or Firm* — Hamilton, Brook, Smith & Reynolds, P.C.

(57) ABSTRACT

The present invention relates to in situ hybridization methods for detecting a target nucleic acid in a biological sample comprising performing one or more method steps (e.g., pretreatment, denaturation, hybridization, washes) at room temperature. The invention further relates to kits for performing such methods.

10 Claims, 5 Drawing Sheets

(5 of 5 Drawing Sheet(s) Filed in Color)

Specification includes a Sequence Listing.

(56) References Cited

OTHER PUBLICATIONS

Written Opinion, for Application No. PCT/US2012/069178, entitled "Methods and Kits for Room Temperature In Situ Detection of a Target Nucleic Acid in a Biological Sample", dated Nov. 7, 2013.
Annex to Invitation to Pay Additional Search Fees—Communication Relating to the Results of the Partial International Search, Application No. PCT/US2012/069178, "Methods and Kits for Room Temperature In Situ Detection of a Target Nucleic Acid in a Biological Sample", dated May 7, 2013.
Aquion-pH tables, "pH of Acids and Bases", downloaded on Oct. 20, 2014 from URL: http://www.aqIon.de/site/191; 3 pages.
Carbonari, M., et al. "Improved Procedure for the Measurement of Telomere Length in Whole Cells by PNA Probe and Flow Cytometry," *Cell Proliferation*, vol. 43, No. 6, pp. 553-561 (2010).
Camerini, A., et al., "Evaluation of HER2 and p53 Expression in Predicting Response to Docetaxel-Based First-Line Chemotherapy in Advanced Breast Cancer," *Journal of Experimental & Clinical Cancer Research*, vol. 30, No. 1, pp. 1-8 (2011).
He, H., et al., "Fluorescence in situ Hybridization of Metaphase Chromosomes in Suspension," *International Journal of Radiation Biology*, vol. 77, No. 7, pp. 787-795 (2001).
SSC buffer, downloaded on Mar. 31, 2015; URL:http://en.wikipedia.org/wiki/SSC_buffer; 1page.
Stratagene Catalog, published by Stratgene, 1101 North Torrey Pines Road, La Jolla, CA 92037; p. 39 (1988).
Non-final Office Action for U.S. Appl. No. 13/701,310, "Methods and Kits for In Situ Detection of Nucleotide Sequences", dated Apr. 6, 2015.
Tanke, H. J., et al., "New Strategy for Multi-Colour Fluorescence in situ *Hybridisation*: COBRA: COmbined Binary RAtio Labelling," *European Journal of Human Genetics*, vol. 7, No. 1, pp. 2-11 (1999).
Notice of Allowance for U.S. Appl. No. 13/712,334, "Methods and Kits for Room Temperature In Situ Detection of a Target Nucleic Acid in a Biological Sample", dated Jun. 29, 2015.
Non-final Office Action for U.S. Appl. No. 13/712,334, "Methods and Kits for Room Temperature In Situ Detection of a Target Nucleic Acid in a Biological Sample", dated Oct. 24, 2014.

\* cited by examiner

SEQUENCE LISTING

<160> NUMBER OF SEQ ID NOS: 19

<210> SEQ ID NO 1
<211> LENGTH: 27
<212> TYPE: DNA
<213> ORGANISM: Homo sapiens

<400> SEQUENCE: 1
ccagtcgaat ccattcgagt acatacc                                      27

<210> SEQ ID NO 2
<211> LENGTH: 27
<212> TYPE: DNA
<213> ORGANISM: Homo sapiens

<400> SEQUENCE: 2 cctttttgaat ccattccatt ggagtcc                                     27

<210> SEQ ID NO 3
<211> LENGTH: 30
<212> TYPE: DNA
<213> ORGANISM: Homo sapiens

```
<400> SEQUENCE: 3
attcattgca ttccgtttca tgaaattcga                                30

<210> SEQ ID NO 4
<211> LENGTH: 30
<212> TYPE: DNA
<213> ORGANISM: Homo sapiens

<400> SEQUENCE: 4
ctgcatacaa tttcactcca ttcgttccca                                30

<210> SEQ ID NO 5
<211> LENGTH: 30
<212> TYPE: DNA
<213> ORGANISM: Homo sapiens

<400> SEQUENCE: 5
tccattggag tcaattcctt tcgacaccca                                30

<210> SEQ ID NO 6
<211> LENGTH: 30
<212> TYPE: DNA
<213> ORGANISM: Homo sapiens

<400> SEQUENCE: 6
ttgatcctat tttattaaat tgcattctat                                30

<210> SEQ ID NO 7
<211> LENGTH: 30
<212> TYPE: DNA
<213> ORGANISM: Homo sapiens

<400> SEQUENCE: 7
gtgcgccctc aactaacagt gttgaagctt                                30

<210> SEQ ID NO 8
<211> LENGTH: 30
<212> TYPE: DNA
<213> ORGANISM: Homo sapiens

<400> SEQUENCE: 8
gaaacgggat tgtcttcata taaactctag                                30

<210> SEQ ID NO 9
<211> LENGTH: 30
<212> TYPE: DNA
<213> ORGANISM: Homo sapiens

<400> SEQUENCE: 9
gtatcttcca ataaaagcta gatagaagca                                30

<210> SEQ ID NO 10
<211> LENGTH: 30
<212> TYPE: DNA
<213> ORGANISM: Homo sapiens

<400> SEQUENCE: 10
atgtcagaaa cttttcatg atgtatctac                                 30

<210> SEQ ID NO 11
<211> LENGTH: 30
<212> TYPE: DNA
<213> ORGANISM: Homo sapiens
```

<400> SEQUENCE: 11
tatgtgtgat gtgcgccctc aactaagagt                                      30

<210> SEQ ID NO 12
<211> LENGTH: 30
<212> TYPE: DNA
<213> ORGANISM: Homo sapiens

<400> SEQUENCE: 12
tctcagaagc ttcattggga tgtttcaatt                                      30

<210> SEQ ID NO 13
<211> LENGTH: 30
<212> TYPE: DNA
<213> ORGANISM: Homo sapiens

<400> SEQUENCE: 13
ggaatacggt gataaaggaa atatcttcca                                      30

<210> SEQ ID NO 14
<211> LENGTH: 30
<212> TYPE: DNA
<213> ORGANISM: Homo sapiens

<400> SEQUENCE: 14
tctttgtgtt gtgtgtactc atgtaacagt                                      30

<210> SEQ ID NO 15
<211> LENGTH: 30
<212> TYPE: DNA
<213> ORGANISM: Homo sapiens

<400> SEQUENCE: 15
tttctgccct acctggaagc ggacatttcg                                      30

<210> SEQ ID NO 16
<211> LENGTH: 30
<212> TYPE: DNA
<213> ORGANISM: Homo sapiens

<400> SEQUENCE: 16
ggttatcttc atataaaatc cagacaggag                                      30

<210> SEQ ID NO 17
<211> LENGTH: 30
<212> TYPE: DNA
<213> ORGANISM: Homo sapiens

<400> SEQUENCE: 17
cggcactacc tggaagtgga tatttcgagc                                      30

<210> SEQ ID NO 18
<211> LENGTH: 30
<212> TYPE: DNA
<213> ORGANISM: Homo sapiens

<400> SEQUENCE: 18
tctgcactac ctggaagagg ccatttcgag                                      30

<210> SEQ ID NO 19
<211> LENGTH: 30
<212> TYPE: DNA

```
<213> ORGANISM: Homo sapiens

<400> SEQUENCE: 19
cctacgggga gaaaggaaat atcttcaaat                                        30
```

METHODS AND KITS FOR ROOM TEMPERATURE IN SITU DETECTION OF A TARGET NUCLEIC ACID IN A BIOLOGICAL SAMPLE

RELATED APPLICATIONS

This application is a divisional of U.S. patent application Ser. No. 13/712,334, filed on Dec. 12, 2012, now U.S. Pat. No. 9,145,584, which claims the benefit of U.S. Provisional Application No. 61/569,656, filed on Dec. 12, 2011.

The entire teachings of the above applications are incorporated herein by reference.

INCORPORATION BY REFERENCE OF MATERIAL IN ASCII TEXT FILE

This application incorporates by reference the Sequence Listing contained in the following ASCII text file being submitted concurrently herewith:

File name: 43731004008SeqList.txt; created Sep. 2, 2015, 3 KB in size.

BACKGROUND OF THE INVENTION

Fluorescence in situ hybridization (FISH) has been employed as a molecular technique to detect DNA sequences on human chromosomes for more than 20 years (Bauman 1985, Acta Histochem Suppl. 31:9-18; Pinkel 1986, PNAS 83(9):2934-8). Over the past two decades, refinement of various aspects of the FISH technique has advanced the field of human cytogenetics and molecular diagnostics, allowing for the identification of chromosomal abnormalities associated with solid tumors and hematopoietic malignancies, and for the diagnosis of infectious diseases. (Heim and Mitelman 1995, Genes Chromosomes Cancer 14(1):56-62; Klinger 1995, Prenat Diagn. 15(1):1-5; Timm, Podniesinski et al. 1995, Cytometry 22(3):250-5; Heselmeyer, Macville et al. 1997, Genes Chromosomes Cancer 19(4):233-40; Sauer, Wiedswang et al. 2003, APMIS 111(3):444-50).

Current FISH procedures are labor intensive and time consuming, requiring multiple manual processing steps and adherence to precise temperature and time requirements. Standard FISH techniques typically require more than a dozen steps to process a slide sample, several of which are performed at different temperatures, necessitating the use of numerous, and often costly, temperature equipment, such as water baths, hot plates, and incubators. These and other limitations of the technique have prevented it from being used more widely in research and clinical laboratories.

Presently, there is a need for more simplified and cost-effective methods of performing FISH that require fewer processing steps, less time and less equipment.

SUMMARY OF THE INVENTION

In one embodiment, the invention relates to a method for detecting a target nucleic acid in a biological sample, comprising the steps of: pretreating a biological sample comprising the target nucleic acid with a solution comprising a protease at a temperature in the range of about 19 degrees Celsius to about 25 degrees Celsius; denaturing the sample; hybridizing at least one probe to the target nucleic acid in the sample, wherein the probe comprises a nucleotide sequence that is substantially complementary to a nucleotide sequence in the target nucleic acid and at least one detectable label; and detecting the at least one detectable label on the oligonucleotide probe following hybridization to the target nucleic acid, thereby detecting the target nucleic acid in the sample.

In another embodiment, the invention relates to a method for detecting a target nucleic acid in a biological sample, comprising the steps of: hybridizing at least one probe to the target nucleic acid in the sample at a temperature in the range of about 19 degrees Celsius to about 25 degrees Celsius, wherein the probe is present in a hybridization buffer comprising about 1-10 mM base and having a pH in the range of about 10 to about 13, and comprises a nucleotide sequence that is substantially complementary to a nucleotide sequence in the target nucleic acid and at least one detectable label; and detecting the at least one detectable label on the probe following hybridization to the target nucleic acid in the sample, thereby detecting the target nucleic acid in the sample.

In another embodiment, the invention relates to a method for detecting a target nucleic acid in a biological sample, comprising the steps of: denaturing a biological sample comprising the target nucleic acid; hybridizing at least one probe to the target nucleic acid in the sample, wherein the probe comprises a nucleotide sequence that is substantially complementary to a nucleotide sequence in the target nucleic acid and at least one detectable label; washing the sample at a temperature in the range of about 19 degrees Celsius to about 25 degrees Celsius in a wash buffer having a pH in the range of about 10 to about 13, the wash buffer comprising about 1-10 mM base and one or more salts at a final concentration of about 0.03 M to about 0.09 M; and detecting the at least one detectable label on probe that has hybridized to the target nucleic acid in the sample, thereby detecting the target nucleic acid in the sample.

In a further embodiment, the invention relates to a method for detecting a target nucleic acid in a biological sample, comprising the steps of: denaturing a biological sample comprising the target nucleic acid by contacting the sample with a solution comprising a base and about 50% to about 80% alcohol; hybridizing at least one probe to the target nucleic acid in the sample, wherein the probe is present in a hybridization buffer comprising about 1-10 mM base and having a pH in the range of about 10 to about 13, and comprises a nucleotide sequence that is substantially complementary to a nucleotide sequence in the target nucleic acid and at least one detectable label; washing the sample in a wash buffer having a pH in the range of about 10 to about 13, the wash buffer comprising about 1-10 mM base and one or more salts at a final concentration of about 0.03 M to about 0.09 M; and detecting the at least one detectable label on probes that have hybridized to the target nucleic acid in the sample, thereby detecting the target nucleic acid in the sample, wherein each of steps a), b) and c) is performed at a temperature in the range of about 19 degrees Celsius to about 25 degrees Celsius.

In yet another embodiment, the invention relates to a method for determining whether a target nucleic acid is present in a biological sample, comprising the steps of: denaturing a biological sample comprising the target nucleic acid; incubating at least one probe with the sample, wherein the probe comprises a nucleotide sequence that is substantially complementary to a nucleotide sequence in the target nucleic acid and at least one detectable label; washing the sample in a wash buffer; and determining whether the target nucleic acid is present in the sample by detecting one or more probes that have hybridized to the target nucleic acid in the sample, wherein at least one of steps a), b) and c) is performed at a temperature in the range of about 19 degrees Celsius to about 25 degrees Celsius.

Any step in the methods described herein can be performed efficiently at room temperature. Accordingly, performing all method steps at room temperature obviates the need for expensive temperature equipment and adherence to precise and variable temperature requirements. Such methods require fewer steps and less time to complete than standard, elevated temperature FISH techniques.

BRIEF DESCRIPTION OF THE DRAWINGS

The patent or application file contains at least one drawing executed in color. Copies of this patent or patent application publication with color drawings will be provided by the Office upon request and payment of the necessary fee.

DETAILED DESCRIPTION OF THE INVENTION

Definitions

Figure 1:
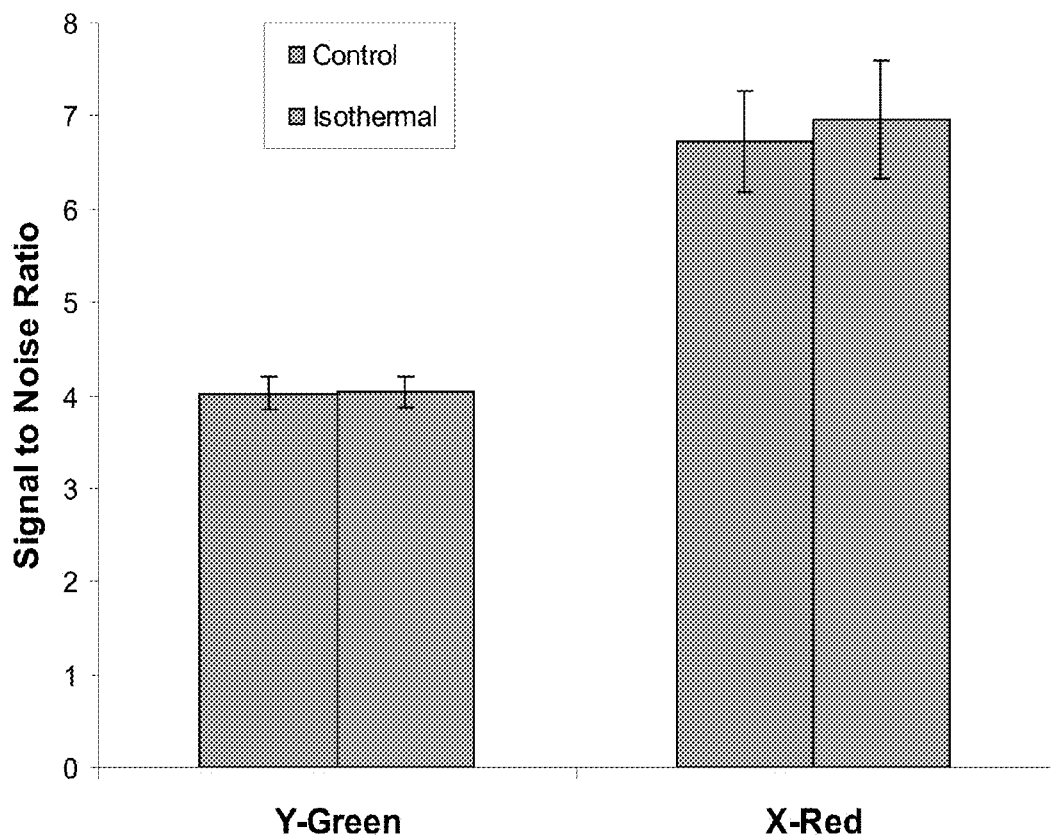
FIG. 1 is a graph depicting a comparison of signal-to-noise ratios (SNR) produced by labeled Y- and X-chromosome oligonucleotide probes following FISH using conventional denaturation conditions (blue) or room temperature denaturation conditions (grey).

Unless defined otherwise, all technical and scientific terms used herein have the same meaning as commonly understood by one of ordinary skill in the art to which this invention pertains.

As used herein, the terms "room temperature" and "RT" refer to temperatures in the range of about 19 degrees Celsius to about 25 degrees Celsius.

A "room-temperature method" or "room temperature procedure" (e.g., "room-temperature FISH"), as used herein, refers to a method in which at least one method step (e.g., denaturation, hybridization, post-hybridization washing) that is typically performed at an elevated temperature (e.g., a temperature greater than 25 degrees Celsius) in a standard, prior art in situ detection method, is performed in the range of about 19 degrees Celsius to about 25 degrees Celsius. Preferably, in the room-temperature methods described herein, at least two, more preferably, at least three, and even more preferably, all, of such method steps are performed in the range of about 19 degrees Celsius to about 25 degrees Celsius. If two or more steps in a "room-temperature method" are performed at room temperature, the temperature at which each of those steps is performed need not be the same, as long as the temperature is in the range of about 19 degrees Celsius to about 25 degrees Celsius.

The term "nucleotide" refers to naturally occurring ribonucleotide or deoxyribonucleotide monomers, as well as non-naturally occurring derivatives and analogs thereof. Accordingly, nucleotides can include, for example, nucleotides comprising naturally occurring bases (e.g., A, G, C, or T) and nucleotides comprising modified bases (e.g., 7-deazaguanosine, or inosine).

The term "sequence," in reference to a nucleic acid, refers to a contiguous series of nucleotides that are joined by covalent bonds (e.g., phosphodiester bonds).

The term "nucleic acid" refers to a polymer having multiple nucleotide monomers. A nucleic acid can be single- or double-stranded, and can be DNA (e.g., cDNA or genomic DNA), RNA, or hybrid polymers (e.g., DNA/RNA). Nucleic acids can be chemically or biochemically modified and/or can contain non-natural or derivatized nucleotide bases. Nucleic acid modifications include, for example, methylation, substitution of one or more of the naturally occurring nucleotides with an analog, internucleotide modifications such as uncharged linkages (e.g., methyl phosphonates, phosphotriesters, phosphoamidates, carbamates, and the like), charged linkages (e.g., phosphorothioates, phosphorodithioates, and the like), pendent moieties (e.g., polypeptides), intercalators (e.g., acridine, psoralen, and the like), chelators, alkylators, and modified linkages (e.g., alpha anomeric nucleic acids, and the like). Nucleic acids also include synthetic molecules that mimic nucleic acids in their ability to bind to a designated sequence via hydrogen bonding and other chemical interactions. Typically, the nucleotide monomers are linked via phosphodiester bonds, although synthetic forms of nucleic acids can comprise other linkages (e.g., peptide nucleic acids (also referred to herein as "PNAs"), such as described in Nielsen et al., Science 254, 1497-1500, 1991). Nucleic acids can also include, for example, conformationally restricted nucleic acids (e.g., "locked nucleic acids" or "LNAs," such as described in Nielsen et al., J. Biomol. Struct. Dyn. 17:175-91, 1999), morpholinos, glycol nucleic acids (GNA) and threose nucleic acids (TNA). "Nucleic acid" does not refer to any particular length of polymer and can, therefore, be of substantially any length, typically from about six (6) nucleotides to about 109 nucleotides or larger. In the case of a double-stranded polymer, "nucleic acid" can refer to either or both strands.

The term "oligonucleotide" refers to a short nucleic acid, typically about 6 to about 100 nucleotide bases in length, joined by covalent linkages, such as phosphorus linkages (e.g., phosphodiester, alkyl and aryl-phosphonate, phosphorothioate, phosphotriester), and/or non-phosphorus linkages (e.g., peptide, sulfamate, and others).

As used herein, the term "genomic fragment" refers to fragments prepared from genomic DNA, including, but not limited to, cloned genomic fragments and amplified genomic fragments (e.g., genomic fragments prepared by PCR amplification).

The term "target nucleic acid" refers to a nucleic acid whose presence or absence in a sample is desired to be detected.

The term "target sequence" refers to a nucleotide sequence in a target nucleic acid that is capable of forming a hydrogen-bonded duplex with a complementary sequence (e.g., a substantially complementary sequence) on an oligonucleotide probe.

As used herein, "complementary" refers to sequence complementarity between two different nucleic acid strands or between two regions of the same nucleic acid strand. A first region of a nucleic acid is complementary to a second region of the same or a different nucleic acid if, when the two regions are arranged in an anti-parallel fashion, at least one nucleotide residue of the first region is capable of base pairing (i.e., hydrogen bonding) with a residue of the second region, thus forming a hydrogen-bonded duplex.

The term "substantially complementary" refers to two nucleic acid strands (e.g., a strand of a target nucleic acid and a complementary single-stranded oligonucleotide probe) that are capable of base pairing with one another to form a stable hydrogen-bonded duplex under stringent hybridization conditions, including the room temperature hybridization conditions described herein. In general, "substantially complementary" refers to two nucleic acids having at least 70%, for example, about 75%, 80%, 85%, 90%, 95%, 97%, 98%, 99% or 100% complementarity.

"Repeat sequence" or "repetitive sequence" refers to noncoding tandemly repeated nucleotide sequences in the human genome including, e.g., repeat sequences from the alpha satellite, satellite 1, satellite 2, satellite 3, the beta satellite, the gamma satellite and telomeres. Repeat sequences are known in the art and are described in e.g., (Allshire et al., Nucleic Acids Res 17(12): 4611-27 (1989); Cho et al., Nucleic Acids Res 19(6): 1179-82 (1991); Fowler et al., Nucleic Acids Res 15(9): 3929 (1987); Haaf et al., Cell 70(4): 681-96 (1992); Lee et al., Chromosoma 109(6): 381-9 (2000); Maeda and Smithies, Annu Rev Genet 20: 81-108 (1986); Meyne and Goodwin, Chromosoma 103(2): 99-103 (1994); Miklos (1985). Localized highly repetitive DNA sequences in vertebrate genomes. Molecular evolutionary genetics. I. J. R. Macintyre. N.Y., Plenum Publishing Corp.: 241-321 (1985); Tagarro et al., Hum Genet 93(2): 125-8 (1994); Waye and Willard, PNAS USA 86(16): 6250-4 (1989); and Willard and Waye, J Mol Evol 25(3): 207-14 (1987). The repeat sequences are located at, e.g., the centromeric, pericentromeric, heterochromatic, and telomeric regions of chromosomes. Consensus repeat sequences are described in, e.g. Willard and Waye, J Mol Evol 25(3): 207-14 (1987) and Tagarro et al., Hum Genet 93(2): 125-8 (1994). Vissel and Choo, Nucleic Acids Res. 15(16): 6751-6752 (1987), Cho et al., Nucleic Acids Res 19(6): 1179-82 (1991).

The term "chromosome-specific nucleic acid sequence," or "chromosome-specific nucleotide sequence," as used herein, refers to a nucleic acid sequence that is specific to a particular chromosome within the genome of a cell.

The term "probe" refers to an oligonucleotide that includes a target-binding region that is substantially complementary to a target sequence in a target nucleic acid and, thus, is capable of forming a hydrogen-bonded duplex with the target nucleic acid. Typically, the probe is a single-stranded probe, having one or more detectable labels to permit the detection of the probe following hybridization to its complementary target.

As used herein, "target-binding region" refers to a portion of an oligonucleotide probe that is capable of forming a hydrogen-bonded duplex with a complementary target nucleic acid.

The term "detectable label," as used herein, refers to a moiety that indicates the presence of a corresponding molecule (e.g., probe) to which it is bound.

An "indirect label" refers to a moiety, or ligand, that is detected using a labeled secondary agent, or ligand-binding partner, that specifically binds to the indirect label.

A "direct label" refers to a moiety that is detectable in the absence of a ligand-binding partner interaction.

The term "biological sample" refers to a material of biological origin (e.g., cells, tissues, organs, fluids).

A "linker," in the context of attachment of two molecules (whether monomeric or polymeric), means a molecule (whether monomeric or polymeric) that is interposed between and adjacent to the two molecules being attached. A "linker" can be used to attach, e.g., oligonucleotide probe sequence and a label (e.g., a detectable label). The linker can be a nucleotide linker (i.e., a sequence of the nucleic acid that is between and adjacent to the non-adjacent sequences) or a non-nucleotide linker.

The term "hybrid" refers to a double-stranded nucleic acid molecule formed by hydrogen bonding between complementary nucleotides.

The term "stringency" refers to hybridization conditions that affect the stability of hybrids, e.g., temperature, salt concentration, pH, formamide concentration, and the like. These conditions are empirically optimized to maximize specific binding, and minimize nonspecific binding, of a probe to a target nucleic acid.

The term "fluorophore" refers to a chemical group having fluorescence properties.

The term "optionally" means that the recited step (e.g., in the case of methods of the invention) or component (e.g., in the case of kits of the invention) may or may not be included.

The present invention is based, in part, on the discovery of a simplified and effective alternative fluorescence in situ hybridization (FISH) technique, referred to herein as "room temperature FISH," wherein sample denaturation, probe hybridization, washes, or any combination thereof, can be performed at room temperature. A comparison between a traditional FISH method and two different room temperature FISH methods of the invention is shown in Table 1. Listed are the different steps needed for completion of the methods, along with the required temperature, apparatus, and times needed for use with oligonucleotide probes. The room temperature methods of the invention obviate the need for expensive precision temperature equipment (e.g., water baths, hotplates, incubators, freezer units) that are typically required for traditional FISH methods.

TABLE 1

Comparison of Traditional FISH and Room Temperature FISH Methods.

| Treatment | Traditional FISH | | | RT FISH | | Fast RT FISH | |
|---|---|---|---|---|---|---|---|
| | Temp (° C.) | Equipment | Time (min) | Temp (° C.) | Time (min) | Temp (° C.) | Time (min) |
| Protease | 37 | Water bath | 5-15* | RT | 5-15* | N/A*** | |
| Wash | RT | N/A | 5 | RT | 5 | | |
| Formaldehyde 1% | RT | N/A | 10 | RT | 10 | | |
| Wash | RT | N/A | 5 | RT | 5 | | |
| 70% Ethanol | RT | N/A | 1 | N/A | N/A | | |
| Denaturation | RT | N/A | N/A | RT | 10 | RT | 10 |
| 85% Ethanol | RT | N/A | 1 | RT | 1 | RT | 1 |
| 100% Ethanol | RT | N/A | 1 | RT | 1 | RT | 1 |
| Air dry | RT | N/A | 5 | RT | 5 | RT | 5 |
| Hybridization | 37 | Hot plate | 5-10** | RT | 5-10** | RT | 5-10** |
| Wash | RT | N/A | 5 | RT | 5 | RT | 5 |
| Wash | 50 | Water bath | 5 | N/A | N/A | N/A | N/A |
| Wash | N/A | N/A | N/A | RT | 5 | RT | 5 |

TABLE 1-continued

Comparison of Traditional FISH and
Room Temperature FISH Methods.

| | Traditional FISH | | | RT FISH | | Fast RT FISH | |
|---|---|---|---|---|---|---|---|
| Treatment | Temp (° C.) | Equipment | Time (min) | Temp (° C.) | Time (min) | Temp (° C.) | Time (min) |
| Wash | RT | N/A | 5 | RT | 5 | RT | 5 |
| Mounting slides | RT | N/A | 10 | RT | 10 | RT | 10 |
| Total time (min) | 58-73 | | | 72-87 | | 47-62 | |

*depending on the cell type or tissue, longer protease time may be required
**depending on the cell type or tissue, longer hybridization time may be required.
***with most cell types, pretreatments are not needed because denaturing reagent permeabilizes cell membranes and partially degrades proteins.
RT = room temperature
N/A = Not applicable Methods for Detecting a Target Nucleic Acid/Methods for Determining Whether a Target Nucleic Acid is Present in a Biological Sample The present invention relates, in one embodiment, to a room-temperature method for determining whether a target nucleic acid is present in a biological sample. In another embodiment, the invention relates to a room temperature method for detecting a target nucleic acid in a biological sample. Exemplary methods of the invention comprise one or more steps performed at room temperature, wherein the steps are selected from the group consisting of denaturing the sample; incubating at least one detectably-labeled probe (e.g., a single stranded oligonucleotide probe, a BAC probe) with the target nucleic acid in the sample; washing the sample to remove unhybridized probe and detecting the detectable label on the probe, thereby detecting the target nucleic acid in the sample, if present. In a preferred embodiment, all steps of the methods described herein are carried out at room temperature, preferably at a temperature of about 21° C.

A detailed description of the various steps of the methods of the invention are set forth herein below.

Sample Preparation/Pre-Treatment

Suitable biological samples for the methods of the invention include, for example, cells (e.g., cell lines, peripheral blood cells, epithelial cells), tissues (formalin-fixed, paraffin-embedded tissues (FFPE)), organs, blood, spinal fluid, lymph fluid, tears, saliva, sputum, urine, semen, amniotic fluid, hair, skin, tumors (e.g., a biopsy). Preferably, the biological sample includes chromosomal DNA. In a particular embodiment, the biological sample employed in the methods of the invention is a cell sample comprising cells of animal (e.g., human) or vegetal origin. Preferably, the cells in the sample comprise one or more of the following cell types: epithelial cells (e.g., urothelial cells, endometrial epithelial cells, exfoliated prostate epithelial cells, colon epithelial cells), peripheral blood cells, skin cells (e.g., cells from FFPE skin tissue sections), bone marrow cells, blastomeres from embryos, sperm cells, oocytes, and polar bodies. Preferably, the biological sample is obtained from a human.

A biological sample can include, in one embodiment, a single target nucleic acid or, in alternative embodiments, multiple target nucleic acids (e.g., two or more distinct target nucleic acids). Target nucleic acids can be DNA or RNA and can include intragenic, intergenic and/or transgenic nucleotide sequences. Thus, target nucleic acids can be endogenous genomic nucleotide sequences or artificial or foreign (e.g., transgenic) nucleotide sequences. Typically, a target nucleic acid comprises a chromosome-specific nucleotide sequence. Exemplary chromosome-specific nucleotide sequences are shown in Table 2.

TABLE 2

Exemplary Chromosome-Specific Nucleic Acid Sequences.

| SEQ ID NO: | NAME | SEQUENCE (5'-3') |
|---|---|---|
| 1 | Y1 | CCAGTCGAATCCATTCGAGTACATACC |
| 2 | Y2 | CCTTTTGAATCCATTCCATTGGAGTCC |
| 3 | Y3 | ATTCATTGCATTCCGTTTCATGAAATTCGA |
| 4 | Y4 | CTGCATACAATTTCACTCCATTCGTTCCCA |
| 5 | Y5 | TCCATTGGAGTCAATTCCTTTCGACACCCA |
| 6 | Y6 | TTGATCCTATTTTATTAAATTGCATTCTAT |
| 7 | 2.1.1 | GTGCGCCCTCAACTAACAGTGTTGAAGCTT |
| 8 | 2.2.2 | GAAACGGGATTGTCTTCATATAAACTCTAG |
| 9 | 2.5.1 | GTATCTTCCAATAAAAGCTAGATAGAAGCA |
| 10 | 2.6.1 | ATGTCAGAAACTTTTTCATGATGTATCTAC |
| 11 | 2.7.3 | TATGTGTGATGTGCGCCCTCAACTAAGAGT |
| 12 | 2.8.4 | TCTCAGAAGCTTCATTGGGATGTTTCAATT |
| 13 | 2.10.1 | GGAATACGGTGATAAAGGAAATATCTTCCA |
| 14 | 4.3.2 | TCTTTGTGTTGTGTGTACTCATGTAACAGT |
| 15 | 4.6.2 | TTTCTGCCCTACCTGGAAGCGGACATTTCG |
| 16 | 4.7.5 | GGTTATCTTCATATAAAATCCAGACAGGAG |
| 17 | 4.10.2 | CGGCACTACCTGGAAGTGGATATTTCGAGC |
| 18 | 4.18.7 | TCTGCACTACCTGGAAGAGGCCATTTCGAG |
| 19 | 4.22.10 | CCTACGGGGAGAAAGGAAATATCTTCAAAT |

Target nucleic acids can include unique or repetitive nucleotide sequences. Preferably, the target nucleic acid includes a repetitive genomic sequence, for example, a repeat sequence of a specific human chromosome (i.e., chromosome 1, 2, 3, 4, 5, 6, 7, 8, 9, 10, 11, 12, 13, 14, 15, 16, 17, 18, 19, 20, 21, 22, the X chromosome or the Y chromosome). Suitable repeat sequences include, but are not limited to, a centromeric repeat sequence, a pericentromeric repeat sequence, a heterochromatin repeat sequence, a telomeric repeat sequence, an alpha satellite repeat sequence, a beta satellite repeat sequence, a gamma satellite repeat sequence, and a satellite 1, 2, or 3 repeat sequence. In some embodiments, the target nucleic acid includes a target sequence of about 20 to about 50 contiguous nucleotides within a specific repeat sequence.

Typically, the biological sample employed in the methods of the invention is a fixed sample (e.g., a fixed cell sample, a fixed tissue sample, a chromosome spread). A variety of suitable fixatives are known in the art and include, for example, acid acetone solutions, various aldehyde solutions (e.g., formaldehyde, paraformaldehyde, and glutaraldehyde) and acid alcohol solutions. Examples of specific fixatives for chromosomal preparations are discussed, for example, in Trask et al. (Science 230:1401-1402, 1985). The biological sample can be prepared (e.g., fixed) in solution, or on a solid support, such as, but not limited to, a microscope slide, a coverslip and a multiwell plate (e.g., a microtitre plate).

In one embodiment, a biological sample is contacted with (e.g., is denatured in) a solution comprising at least one base (e.g., NaOH) and at least one alcohol (e.g., ethanol) prior to incubating a probe with the sample. By contacting the sample with the solution comprising the base and alcohol, the nucleic acids in the sample become denatured, rendering the target nucleic acid more accessible to a complementary probe. In certain types of biological samples (e.g., sperm cells), the solution comprising the base and alcohol may also decondense the chromosomes in the sample, further promoting accessibility of a target nucleic acid to a complementary probe.

Suitable bases for use in the methods of the invention include, without limitation, potassium hydroxide, barium hydroxide, caesium hydroxide, sodium hydroxide, strontium hydroxide, calcium hydroxide, lithium hydroxide, rubidium hydroxide, magnesium hydroxide, butyl lithium, lithium diisopropylamide, lithium diethylamide, sodium amide, sodium hydride, lithium bis(trimethylsilyl)amide, sodium carbonate and ammonia, or a combination thereof. Preferably, the base is an alkali base. More preferably, the base is sodium hydroxide. Suitable concentrations of base in the base/alcohol solution employed in the methods of the invention are typically in the range of about 0.03 normal (N) to about 0.17 N, for example, about 0.05 N, about 0.06 N, about 0.07 N, about 0.08 N, about 0.09 N or about 0.1 N. In a particular embodiment, the solution comprises about 0.07 N NaOH, which is equivalent to 0.07 M NaOH.

Exemplary alcohols for use in the methods of the invention include, for example, ethanol, methanol, propanol, butanol, pentanol and isoamyl alcohol, among others, or mixtures thereof. In a particular embodiment, the solution comprises ethanol. Preferably, the base/alcohol solution comprises about 0.07 N base and about 70% ethanol. The alcohol can be present in the solution at a concentration of about 50% to about 90% by volume, for example about 60%, about 70% or about 80% by volume. Preferably, the alcohol is present at a concentration of about 70% by volume.

The biological sample is typically contacted with the base/alcohol solution for a time period ranging from about 3 minutes to about 20 minutes, preferably about 11 minutes to about 17 minutes, more preferably about 13 minutes to about 15 minutes. In a particular embodiment, the sample is incubated in the base/alcohol solution at a temperature in the range of about 19° C. to about 25° C., preferably about 20° C. to about 22° C., more preferably about 21° C.

In another embodiment, the biological sample is denatured in a non-alkaline denaturation buffer (e.g., 70% formamide) at an elevated temperature (e.g., 72° C.).

The methods of the invention can optionally include one or more additional steps generally employed in conventional in situ hybridization procedures to make nucleic acids in a sample more accessible to probes (e.g., pretreatment steps). Such steps include, for example, treating a biological sample with one or more proteinases (e.g., proteinase K, trypsin, pepsin, collagenase) and/or mild acids (e.g., 0.02-0.2 N HCl, 25% to 75% acetic acid). An optional pretreatment with RNase can also be utilized to remove residual RNA from the biological sample. Other optional pre-treatment steps include fixation with formaldehyde or paraformaldehyde, detergent permeabilization, heat denaturation and aging of the sample.

In one embodiment, the methods of the invention include the optional step of treating (e.g., pretreating, digesting) the biological sample with one or more proteases (e.g., pepsin) at a temperature in the range of about 19° C. to about 25° C., preferably about 20° C. to about 22° C., more preferably about 21° C., prior to denaturing the sample. The protease is preferably present in a buffer at a concentration in the range of about 0.1% to about 0.3%. Preferably, the buffer is an acidic buffer. Suitable pretreatment buffers for use in the methods of the invention include, but are not limited to, 0.01 N HCl. Typically, the biological sample is treated (e.g., pretreated, digested) with protease for about 5 minutes to about 20 minutes. In a particular embodiment, the biological sample is pretreated with pepsin in 0.01 N HCl for about 15 minutes.

Probe Hybridization

The methods of the invention further comprise the step of incubating at least one probe (e.g., an oligonucleotide) with the sample at room temperature under conditions suitable for hybridizing the probe to the target nucleic acid when the target nucleic acid is present in the sample. For example, hybridization can be performed at a temperature in the range of about 19° C. to about 25° C., preferably about 20° C. to about 22° C., more preferably about 21° C. Generally, hybridization is performed under conditions (e.g., temperature, incubation time, salt concentration, etc.) sufficient for a probe to hybridize with a complementary target nucleic acid in a biological sample. Suitable hybridization buffers and conditions for in situ hybridization techniques are generally known in the art. (See, e.g., Sambrook and Russell, supra; Ausubel et al., supra. See also Tijssen, Laboratory Techniques in Biochemistry and Molecular Biology, Vol. 24: Hybridization with Nucleic Acid Probes (Elsevier, N Y 1993)). For example, a hybridization buffer comprising formamide, dextran sulfate and saline sodium citrate (SSC) can be employed in the methods of the invention. Suitable concentrations of formamide in the hybridization buffer include, for example, concentrations in the range of about 20% to about 90% by volume, e.g., about 60%, about 70%, or about 80% by volume. Suitable concentrations of dextran sulfate in a hybridization buffer include, for example, about 3% to about 20%. Suitable concentrations of SSC in a hybridization buffer include, for example, about 0.1× to about 4×. The concentration of total salt in the hybridization buffer is preferably in the range of about 0.03M to about 0.09M.

In a particular embodiment, the hybridization step is performed under alkaline conditions. For example, a hybridization buffer containing one or more bases (e.g., NaOH) and having a pH of about 10 to about 13, preferably about 11 to about 12, is employed. Any of the bases described herein as being suitable for use in the base and alcohol denaturation solution can also be used in the hybridization buffer. Suitable alkaline hybridization buffers that can be employed in the methods of the invention include, for example, about 20-60% formamide, about 5-40% dextran sulfate and about 1-10 mM NaOH, and have a pH in the range of about 10 to about 13. Preferably, the alkaline hybridization buffer contains about 30-50% formamide, about 10% dextran sulfate and about 1-3 mM NaOH, and has a pH in the range of about 11 to about 12. Such conditions are particularly suitable when repetitive sequence probes (e.g., oligonucleotide probes) are employed in the methods described herein. An exemplary hybridization buffer for use in the methods of the invention when unique-sequence probes (e.g., BAC probes) are employed, includes, for example, about 4.2 mM NaOH, about 42% formamide and about 28% dextran sulfate.

Optimal hybridization conditions for a given target sequence and its complementary probe will depend upon several factors such as salt concentration, incubation time, and probe concentration, composition, and length, as will be appreciated by those of ordinary skill in the art. Based on these and other known factors, suitable binding conditions can be readily determined by one of ordinary skill in the art and, if necessary, optimized for use in accordance with the present methods. Typically, hybridization is carried out under stringent conditions that allow specific binding of substantially complementary nucleotide sequences. Stringency can be increased or decreased to specifically detect target nucleic acids having 100% complementarity or to detect related nucleotide sequences having less than 100% complementarity (e.g., about 70% complementarity, about 80% complementarity, about 90% complementarity). Factors such as the length and nature (DNA, RNA, base composition) of the probe sequence, nature of the target nucleotide sequence (DNA, RNA, base composition, presence in solution or immobilization) and the concentration of salts and other components in the hybridization buffer (e.g., the concentration of formamide, dextran sulfate, polyethylene glycol and/or salt) in the hybridization buffer/solution can be varied to generate conditions of either low, medium, or high stringency. These conditions can be varied based on nucleotide base composition and length and circumstances of use, either empirically or based on formulas for determining such variation (see, e.g., Sambrook et al., supra; Ausubel et al., supra).

In certain embodiments, a population (e.g., cocktail) of two or more probes are incubated with a sample. Generally, the probe cocktail composition includes a plurality of different labeled probes, each different labeled probe having (a) a different chromosome-specific sequence and (b) a different detectable label that is distinguishable from the detectable labels on the other probes in the cocktail that are specific for a different chromosome. In some embodiments, the detectable labels on the probes are fluorophores having spectrally distinguishable emission wavelengths. Through the use of different probes labeled with distinguishable markers, such as spectrally distinguishable fluorophores, combinations of probes can be employed at the same time in order to examine the presence or absence of two or more target nucleic acids (e.g., on two or more different chromosomes) in a sample. Hybridization and washing conditions can be adjusted as appropriate for differing detectable markers.

Probes that are useful in the methods of the invention comprise a target binding region consisting of a nucleotide sequence that is substantially complementary to a nucleotide sequence (e.g., a target sequence) in a target nucleic acid in the sample. Although generally desirable, a target binding region in a probe is not required to have 100% complementarity to the target nucleic acid. For example, in some embodiments, probes useful in the methods of the invention can comprise a nucleotide sequence that is at least about 70%, e.g., about 80%, about 90%, about 95% or about 99%, complementary to a nucleotide sequence in a target nucleic acid.

Suitable probes for use in the methods of the invention include, but are not limited to, DNA probes, cDNA probes, RNA probes, peptide nucleic acid (PNA) probes, locked nucleic acid (LNA) probes, morpholino probes, glycol nucleic acid (GNA) probes and threose nucleic acids (TNA) probes. Such probes can be chemically or biochemically modified and/or may contain non-natural or derivatized nucleotide bases. For example, a probe may contain modified nucleotides having modified bases (e.g., 5-methyl cytosine) and/or modified sugar groups (e.g., 2'O-methyl ribosyl, 2'O-methoxyethyl ribosyl, 2'-fluoro ribosyl, 2'-amino ribosyl). Although linear probes are preferred, useful probes can be circular or branched and/or include domains capable of forming stable secondary structures (e.g., stem- and -loop and loop-stem-loop hairpin structures).

Probes that are suitable for use in in situ hybridization methods, including the methods of the invention, are well known in the art and include, for example, oligonucleotide probes (e.g., synthetic oligonucleotides), probes prepared using genomic fragments (e.g., cloned genomic fragments, amplified genomic fragments), and whole genomes arrays (e.g., comparative genomic hybridization arrays).

In a particular embodiment, the probes used in the present invention are oligonucleotide probes (e.g., single stranded DNA oligonucleotide probes). Typical oligonucleotide probes useful in the methods of the invention are linear and range in size from about 20 to about 100 nucleotides, preferably, about 30 to about 50 nucleotides. In a particular embodiment, oligonucleotide probes that are about 30 nucleotides in length are employed in the methods of the invention. Oligonucleotide probes targeting repetitive genomic DNA sequences are preferred.

In another embodiment, the probes used in the present invention are prepared from genomic fragments. Such genomic fragments can be obtained by a variety of procedures, including, but not limited to, amplification of genomic DNA (e.g., by polymerase chain reaction (PCR), such as long-range PCR), nuclease digestion of cloned DNA fragments present in, for example, plasmids, cosmids, artificial chromosomes (e.g., bacterial artificial chromosomes (BACs), yeast artificial chromosomes (YACs), P1-derived artificial chromosomes and mammalian artificial chromosomes) and phages, microdissection of chromosomes, and sorting of whole chromosomes by flow cytometry. Preferably, the probes prepared from genomic fragments target unique, non-repetitive genomic sequences.

Methods of producing probes useful in the methods of the invention are well known in the art and include, for example, biochemical, recombinant, synthetic (e.g., chemical synthesis) and semi-synthetic methods. In one embodiment, the oligonucleotide probes employed in the methods of the invention are produced by chemical synthesis. A synthetic oligonucleotide probe can be produced using known methods for nucleic acid synthesis (see, e.g., Glick and Pasternak, Molecular Biotechnology: Principles and Applications of Recombinant DNA (ASM Press 1998)). For example, solution or solid-phase techniques can be used. Synthesis procedures are typically automated and can include, for example, phosphoramidite, phosphite triester, H-phosphate, or phosphotriester methods.

Probes useful in the methods of the invention can further comprise one or more detectable labels. Labels suitable for use according to the present invention are known in the art and generally include any molecule that, by its chemical nature, and whether by direct or indirect means, provides an identifiable signal allowing detection of the probe. Thus, for example, probes may be labeled in a conventional manner, such as with specific reporter molecules, fluorophores, radioactive materials, or enzymes (e.g., peroxidases, phosphatases). In a particular embodiment, the probes employed in the methods of the invention include one or more fluorophores as detectable labels.

Detectable labels suitable for attachment to probes can be indirect labels or direct labels. Exemplary indirect labels include, e.g., haptens, biotin, or other specifically bindable ligands. For indirect labels, the ligand-binding partner typically has a direct label, or, alternatively, is also labeled indirectly. Examples of indirect labels that are haptens include dinitrophenol (DNP), digoxigenin, biotin, and various fluorophores or dyes (e.g., fluorescein, DY490, DY590, Alexa 405/Cascade blue, Alexa 488, Bodiby FL, Dansyl, Oregon Green, Lucifer Yellow, Tetramethylrhodamine/Rhodamine Red, and Texas Red). As an indirect label, a hapten is typically detected using an anti-hapten antibody as the ligand-binding partner. However, a hapten can also be detected using an alternative ligand-binding partner (e.g., in the case of biotin, anti-biotin antibodies or streptavidin, for example, can be used as the ligand-binding partner). Further, in certain embodiments, a hapten can also be detected directly (e.g., in the case of fluorescein, an anti-fluorescein antibody or direct detection of fluorescence can be used).

Exemplary "direct labels" include, but are not limited to, fluorophores (e.g., fluorescein, rhodamine, Texas Red, phycoerythrin, Cy3, Cy5, DY fluors (Dyomics GmbH, Jena, Germany) Alexa 532, Alexa 546, Alexa 568, or Alexa 594). Other direct labels can include, for example, radionuclides (e.g., 3H, 35S, 32P, 125I, and 14C), enzymes such as, e.g., alkaline phosphatase, horseradish peroxidase, or β-galactosidase, chromophores (e.g., phycobiliproteins), luminescers (e.g., chemiluminescers and bioluminescers), and lanthanide chelates (e.g., complexes of Eu3+ or Tb3+). In the case of fluorescent labels, fluorophores are not to be limited to single species organic molecules, but include inorganic molecules, multi-molecular mixtures of organic and/or inorganic molecules, crystals, heteropolymers, and the like. For example, CdSe—CdS core-shell nanocrystals enclosed in a silica shell can be easily derivatized for coupling to a biological molecule (Bruchez et al., *Science,* 281:2013-2016, 1998). Similarly, highly fluorescent quantum dots (zinc sulfide-capped cadmium selenide) have been covalently coupled to biomolecules for use in ultrasensitive biological detection (Warren and Nie, *Science,* 281: 2016-2018, 1998).

Probe labeling can be performed, e.g., during synthesis or, alternatively, post-synthetically, for example, using 5'-end labeling, which involves the enzymatic addition of a labeled nucleotide to the 5'-end of the probe using a terminal transferase. A single labeled nucleotide can be added by using a "chain terminating" nucleotide. Alternatively, non-terminating nucleotides can be used, resulting in multiple nucleotides being added to form a "tail." For synthesis labeling, labeled nucleotides (e.g., phosphoramidite nucleotides) can be incorporated into the probe during chemical synthesis. Labels can be added to the 5', 3', or both ends of the probe (see, e.g., U.S. Pat. No. 5,082,830), or at base positions internal to the ODN.

Other methods for labeling nucleic acids utilize platinum-based labeling. Such methods include the Universal Linkage System (ULS, Kreatech Biotechnology B.V., Amsterdam, Netherlands). Platinum based labeling methods and their applications are described in, for example, U.S. Pat. Nos. 5,580,990, 5,714,327, and 6,825,330; International Patent Publication Nos. WO 92/01699, WO 96/35696, and WO 98/15546; Hernandez-Santoset et al., Anal. Chem. 77:2868-2874, 2005; Raap et al., BioTechniques 37:1-6, 2004; Heetebrij et al., ChemBioChem 4:573-583, 2003; Van de Rijke et al., Analytical Biochemistry 321:71-78, 2003; Gupta et al., Nucleic Acids Research 31:e13, 2003; Van Gijswijk et al., Clinical Chemistry 48:1352-1359, 2002; Alers et al., Genes, Chromosomes & Cancer 25:301-305, 1999; Wiegant et al., Cytogenetics and Cell Genetics 87:7-52, 1999; Jelsma et al., Journal of NIH Research 5:82, 1994; Van Belkum et al., BioTechniques 16:148-153, 1994; and Van Belkum et al., Journal of Virological Methods 45:189-200, 1993.

Labeled nucleotide(s) can also be attached to a probe using a crosslinker or a spacer. Crosslinkers may be homo-bifunctional or heterobifunctional. Suitable homobifunctional crosslinkers include, e.g., amine reactive crosslinkers with NHS esters at each end (including, e.g., dithiobis (succinimidylproponate) (DSP); 3,3'-dithiobis(sulfosuccinimidylpropionate) (DTSSP); disuccinimidyl suberate (DSS); Bis(sulfosuccinimidyl)suberate (BS3); Ethylene glycolbis(succinimidylsuccinate) (EGS); Ethylene glycolbis (sulfosuccinimidylsuccinate) (SulfoEGS)); amine reactive crosslinkers with imidoesters at both ends (including, e.g., dimethyl adipimidate (DMA); dimethyl pimelimidate (DMP); dimethyl suberimidate (DMS); dimethyl 3,3'-dithiobispropionimidate (DTBP)); sulfhydryl reactive crosslinkers with dithiopyridyl groups at each end (including, e.g., 1,4-di-[3'-(2'-pyridyldithio)propionamdo]butane (DP-DPB)); sulfhydryl reactive crosslinkers with maleimide groups at each end (including, e.g., bismaleimidohexane (BMH)); carboxyl reactive crosslinkers with hydrazide groups at each end (including, e.g., adipic acid dihydrazide and carbonhydrazide); multi-group reactive crosslinkers with epoxide groups at each end (including, e.g., 1,2:3,4-diepoxybutane; 1,2:5,6-diepoxyhexane; Bis(2,3-epoxypropyl)ether; 1,4-(butanediol)diglycidyl ether). Suitable heterobifunctional crosslinkers include crosslinkers with an amine reactive end and a sulfhydryl-reactive end (including, e.g., N-Succinimidyl 3-(2-pyridyldithio)propionate (SPDP); long chain SPDP (SPDP); Sulfo-LC-SPDP; Succinimidyloxycarbonyl-α-methyl-α-(2-pyridydithio)toluene (SMPT); Sulfo-LC-SMPT; Succinimidyl-4-(N-maleimidomehyl)cyclohexane (SMCC); Sulfo-SMCC; Succinimidyl 6-((iodoacetyl)amino)hexanoate (SIAX); Succinimidyl 6-(6-(((4-iodoacetyl)amino)hexanoyl)amino)hexanoate (SI-AXX)); crosslinkers with a carbonyl-reactive end and a sulfhydryl reactive end (including, e.g., 4-(4-N-Maleimidophenyl)butyric acid hydrazide (MPBH); 4-(N-Maleimidomethyl)cyclohexane-1-carboxyl-hydrazide hydrochloride (M2C2H); 3-(2-Pyridyldithio)propinyl hydrazide (PDPH)); crosslinkers with an amine-reactive end and a photoreactive end (including, e.g., Sulfosuccinimidyl-2-(p-azidosalicylicylamido)ethyl-1,3'-dithiopropionate (SASD); Sulfosuccinimidyl 2-(7-azido-4-methylcoumarin-3-acet-amide)ethyl-1,3'-dithiopropionate (SAED)); crosslinkers with a sulfhydryl-reactive end and a photoreactive end (including, e.g., N-[4-p-Azidosalicylamido)butyl]-3'-(2'pyridyldithio)propionamide (APDP)); crosslinkers with a carbonyl-reactive end and a photoreactive end (including, e.g., 4-(p-Azidosalicylamido)butlyamine (ASBA)). Suitable spacers include, 5' ODN modifications such as dNTP's; and amine-reactive spacers such as amino- or sulfo-phosphoramidites including, e.g., butylphosphoramidites, pentylphosphoramidites, hexylphosphoramidites, heptylphosphoramidites, octylphosphoramidites, nonylphosphoramidites, decylphosphoramidites, undecylphosphoramidites, dodecylphosphoramidites, pentadecylphosphoramidites, octadecylphosphoramidites. Other suitable amine-reactive spacers include e.g., activated polyethylene glycol (PEG) such as (monomethoxy)n glycol, wherein n=3-18 unit repeats. Additional suitable crosslinkers and spacers are set forth in Herman. "Bioconjugate Chemistry". Academic Press. New York, N.Y. 1996.

Washes, Counter-Staining and Mounting

Typically, in situ hybridization techniques employ a series of successive wash steps following the hybridization step to remove unbound and/or non-specifically bound probe from the sample. Such wash steps can be performed in the room temperature methods of the invention. For example, following hybridization of probe to the sample, the hybridized sample can be washed in a solution of appropriate stringency to remove unbound and/or non-specifically bound probes. An appropriate stringency can be determined by washing the sample in successively higher stringency solutions and reading the signal intensity between each wash. Analysis of the data sets in this manner can reveal a wash stringency above which the hybridization pattern is not appreciably altered and which provides adequate signal for the particular probes of interest.

Suitable wash buffers for in situ hybridization methods are generally known in the art (See, e.g., Sambrook and Russell, supra; Ausubel et al., supra. See also Tijssen, Laboratory Techniques in Biochemistry and Molecular Biology, Vol. 24: Hybridization with Nucleic Acid Probes (Elsevier, NY 1993)) and typically include, but are not limited to, one or more salts (e.g., sodium salts, lithium salts, potassium salts). In some embodiments, the wash buffer may also include one or more bases (e.g., NaOH). In other embodiments, the wash buffer may further include one or more detergents (e.g., an ionic detergent, a non-ionic detergent). Suitable detergents for a wash buffer include, for example, sodium dodecyl sulfate (SDS), Triton® X-100, Tween® 20, NP-40, or Igepal CA-630. Preferably, the wash buffer comprises a base (e.g., NaOH) having a concentration of about 0.5 mM to about 5 mM and one or more salts (e.g., sodium citrate) having a total concentration of about 0.03M to about 0.09M.

In a particular embodiment, the wash step(s) in the methods of the invention are performed under alkaline conditions. For example, a wash buffer containing one or more bases (e.g., NaOH) and having a pH of between about 10 and 13, preferably between about 11 and 12, can be employed. Any of the bases described herein as being suitable for use in the base and alcohol denaturation solution may also be used in the wash buffer. Suitable alkaline wash buffers that may be employed in the methods described herein include, for example, about 1×-5×SSC and about 1-10 mM base. In one embodiment (e.g., when repetitive sequence probes, for example, oligonucleotide probes, are employed), the alkaline wash buffer preferably contains about 2×SSC and about 1.75 mM NaOH, and has a pH of about 11. In another embodiment (e.g., when unique sequence probes, for example, BAC probes are employed), the alkaline wash buffer preferably contains about 2×SSC and about 3 mM NaOH.

The number of washes and duration of each wash can be readily determined by one of ordinary skill in the art. Exemplary alkaline wash conditions for the room temperature methods of the invention include, for example, one or more post-hybridization washes in 2×SSC/1.75 mM NaOH, pH 11.0 at room temperature (e.g, about 21° C.) for at least about 2 minutes per wash, preferably, for about 5 minutes per wash. Exemplary non-alkaline wash conditions for the room temperature methods of the invention include, for example, an initial post-hybridization wash in 2×SSC for 5 min. at room temperature (e.g, about 21° C.) followed by one or more washes in 0.03M to 0.09M monovalent salt (e.g., SSC) and 0.1% SDS at room temperature for at least about 2 minutes per wash, preferably, in the range of about 2 minutes to about 5 minutes per wash.

After the sample has been subjected to post-hybridization washes, chromosomal DNA in the sample is preferably counter-stained with a spectrally distinguishable DNA specific stain such as, for example, 4',6-diamidino-2-phenylindole (DAPI), propidium iodide (PI) or a Hoechst reagent/dye and mounted using an antifade reagent. The DNA stain can be added directly to the antifade reagent or can be incubated with the sample, drained and rinsed before the antifade reagent is added. Reagents and techniques for counterstaining and mounting samples are generally known in the art.

Detection of Target Nucleic Acids

The room temperature methods of the invention further include detecting one or more target nucleic acids in the sample. The target nucleic acid is detected by detecting a labeled probe that has hybridized to the target nucleic acid. Detection of the probe label can be accomplished using an approach that is suitable for the particular label, which can be readily determine by those of ordinary skill in the art. For example, fluorophore labels can be detected by detecting the emission wavelength of the particular fluorophore used. Typical methods for detecting fluorescent signals include, e.g., spectrofluorimetry, epifluorescence microscopy, confocal microscopy, and flow cytometry analysis. Fluorescent labels are generally preferred for detection of low levels of target because they provide a very strong signal with low background. Furthermore, fluorescent labels are optically detectable at high resolution and sensitivity through a quick scanning procedure, and different hybridization probes having fluorophores with different emission wavelengths (e.g., fluorescein and rhodamine) can be used for a single sample to detect multiple target nucleic acids.

In the particular case of FISH procedures, which utilize fluorescent probes, a variety of different optical analyses can be utilized to detect hybridization complexes. Spectral detection methods are discussed, for example, in U.S. Pat. No. 5,719,024; Schroeck et al. (Science 273:494-497, 1996); and Speicher et al. (Nature Genetics 12:368-375, 1996). Further guidance regarding general FISH procedures are discussed, for example, in Gall and Pardue (Methods in Enzymology 21:470-480, 1981); Henderson (International Review of Cytology 76:1-46, 1982); and Angerer et al. in Genetic Engineering: Principles and Methods (Setlow and Hollaender eds., Plenum Press, New York, 1985).

Detection of indirect labels typically involves detection of a binding partner, or secondary agent. For example, indirect labels such as biotin and other haptens (e.g., digoxigenin (DIG), DNP, or fluorescein) can be detected via an interaction with streptavidin (i.e., in the case of biotin) or an antibody as the secondary agent. Following binding of the probe and target, the target-probe complex can be detected by using, e.g., directly labeled streptavidin or antibody. Alternatively, unlabeled secondary agents can be used with a directly labeled "tertiary" agent that specifically binds to the secondary agent (e.g., unlabeled anti-DIG antibody can be used, which can be detected with a labeled second antibody specific for the species and class of the primary antibody). The label for the secondary agent is typically a non-isotopic label, although radioisotopic labels can be used. Typical non-isotopic labels include, e.g., enzymes and fluorophores, which can be conjugated to the secondary or tertiary agent. Enzymes commonly used in DNA diagnostics include, for example, horseradish peroxidase and alkaline phosphatase.

Detection of enzyme labels can be accomplished, for example, by detecting color or dye deposition (e.g., p-nitrophenyl phosphate or 5-bromo-4-chloro-3-indolyl phosphate/nitroblue tetrazolium for alkaline phosphatase and 3,3'-diaminobenzidine-NiCl2 for horseradish peroxidase), fluorescence (e.g., 4-methyl umbelliferyl phosphate for alkaline phosphatase) or chemiluminescence (e.g., the alkaline phosphatase dioxetane substrates LumiPhos 530 from Lumigen Inc., Detroit Mich. or AMPPD and CSPD from Tropix, Inc.), depending on the type of enzymatic label employed. Chemiluminescent detection can be carried out with X-ray or Polaroid film or by using single photon counting luminometers (e.g., for alkaline phosphatase labeled probes).

In certain embodiments, digital enhancement or integration is used to detect a signal from a label on a probe. For example, detection of the label can include the use of microscopic imaging using a CCD camera mounted onto the eyepiece tube of a microscope (e.g., a binocular, monocular, or stereo microscope). In some embodiments, detection of the label is accomplished using image scanning microscopy. For example, recent advances in computerized image scanning microscopy have significantly increased the ability to detect rare cells using fluorescence microscopy, permitting detection of 1 positive cell in an environment of ~$6 \times 10^5$ negative cells (see, e.g., Mehes et al., Cytometry 42:357-362, 2000). Advanced image scanning software has been developed that can not only detect multiple colors but also fused or co-localized signals useful for, e.g., detection of translocations on the DNA level (MetaSystems Group, Inc.) Scanning speed typically depends on the number of parameters utilized for reliable detection of single positive cells. Image scanning also allows for images of the cells scored positive to be manually examined for confirmation. Advanced image scanning software for automated, slide-based analysis has been developed that can not only detect multiple colors but also fused or co-localized signals useful for, e.g., detection of translocations on the DNA level (Meta System Group, Inc.) Scanning speed typically depends on the number of parameters utilized for reliable detection of single positive cells. Automated slide-based scanning systems are particularly amenable to high throughput assays.

In one embodiment, scanning slide microscopy, e.g., employing a MetaCyte Automated Bio-Imaging System (Meta System Group, Inc.), is used. This system consists of the following components: 1) Carl Zeiss Axio Plan 2 MOT fluorescence microscope, 2) scanning 8-position stage, 3) PC Pentium III Processor, 4) Jai camera, 5) camera interface, 6) stage control, 7) trackball and mouse, and 8) printer. The focus analysis begins with a slide set-up loaded onto the microscope. The slide is scanned as the stage is moved and the image is captured. Following scanning of the entire slide, a gallery is created. Based on the criterion set up for positive or negative, the image analysis either results in a positive or negative signal. If negative, the slide is rescanned for rare event analyses. If positive, there is a filter change for the appropriate fluorescent signal and 5-7 planes are captured and analyzed. There is walk away/overnight operation for 8 slides (standard or 100 slides with optional tray changer). Adaptive detection algorithms and automatic exposure control function compensate for non-uniform staining conditions. Several markers can be detected simultaneously. The standard light source covers a wide spectrum from UV to IR. Scanning speed up to 1,000 cells per second can be used for rare cell detection if cellular fluorescent intensity allows detection in $\frac{1}{1,000}$ sec. For strong signals, a lower magnification can be used to increase scanning speed.

Alternatively, detection of the probe can be performed in the absence of digital enhancement or integration.

Kits for Detecting Target Nucleic Acids

In another embodiment, the invention relates to kits for detecting a target nucleic acid (e.g., one or more target nucleic acids) in a biological sample under room temperature conditions. Typically, the kits include one or more probes, a denaturation buffer, a hybridization buffer, and a wash buffer. In some embodiments, the kits may include additional, optional components, such as, for example, a secondary detection reagent, a stain for chromosomal DNA, an antifade reagent, instructions, protocols or a combination thereof. Typically, the kits are compartmentalized for ease of use and may include one or more containers with reagents. In one embodiment, all of the kit components are packaged together. Alternatively, one or more individual components of the kit may be provided in a separate package from the other kits components (e.g., the denaturation buffer may be packaged separately from the other kits components).

In one embodiment, the kits of the invention include, in one container, at least one single-stranded oligonucleotide probe that comprises a target binding region that is substantially complementary to a target sequence in a target nucleic acid. Preferably, each single-stranded oligonucleotide probe in the kits of the invention is a chromosome-specific probe. The single-stranded oligonucleotide probe typically consists of about 20 to about 50 nucleotides, preferably about 30 nucleotides. Suitable types of oligonucleotide probes (e.g, DNA, RNA, PNA) for use in the kits of the invention are described herein. Preferably, the oligonucleotide probes in the kits of the invention are DNA probes.

In certain embodiments, the single-stranded oligonucleotide probes in the kits of the invention are labeled (e.g., comprise one or more detectable labels). Exemplary detectable labels for single-stranded oligonucleotide probes are described herein. Preferably, the oligonucleotide probes in the kits of the invention comprise one or more fluorophores (e.g., fluorescein, rhodamine, Texas Red, phycoerythrin, Cy3, Cy5, Alexa 532, Alexa 546, Alexa 568, or Alexa 594).

In some embodiments, the kits of the invention include a plurality of different labeled probes, either mixed in the same container as a probe cocktail composition, or provided in separate containers. In such embodiments, each probe is specific for a particular target nucleic acid and comprises a detectable label that is distinguishable from the detectable labels present on other probes in the cocktail or kit that have specificity for different target nucleic acids. For example, each probe can comprise a fluorophore having a spectrally distinguishable emission wavelength. Suitable fluorophores for use in the kits of the invention having a plurality of different labeled probes include, e.g., Alexa 488 (excitation maximum at 492 nm and emission maximum at 520 nm) and Alexa 546 (excitation maximum at 555 nm and emission maximum at 570 nm)).

In one embodiment, the kits of the invention include, in a separate container, a denaturation buffer that comprises a base (e.g., NaOH) and an alcohol. The denaturation buffer preferably includes about 0.03N to about 0.17N base, for example, about 0.05N, about 0.06N, about 0.07N, about 0.08N, about 0.09N or about 0.1N base. Preferably, the denaturation buffer comprises about 0.07N NaOH (i.e., 0.07M NaOH). Exemplary bases for use in the denaturation buffer include, for example, potassium hydroxide, barium hydroxide, caesium hydroxide, sodium hydroxide, strontium hydroxide, calcium hydroxide, lithium hydroxide, rubidium hydroxide, magnesium hydroxide, butyl lithium, lithium diisopropylamide, lithium diethylamide, sodium amide, sodium hydride, lithium bis(trimethylsilyl)amide, sodium carbonate and ammonia, or a combination thereof. Preferably, the base is an alkali base. More preferably, the base is sodium hydroxide. The denaturation buffer further includes at least one alcohol at a concentration of about 50% to about 90% by volume, for example about 60%, about 70% or about 80% by volume. Preferably, the alcohol is present at a concentration of about 70% by volume. Exemplary alcohols for use in the denaturation buffer include, for example, ethanol, methanol, propanol, butanol, pentanol and isoamyl alcohol, among others, or mixtures thereof. In a particular embodiment, the denaturation buffer comprises about 70% ethanol.

In yet another embodiment, the denaturation buffer comprises formamide (e.g., 70% formamide) instead of alcohol or base.

In another container, the kits of the invention include a hybridization buffer. In one embodiment, the hybridization buffer comprises one or more bases (e.g., NaOH) and has a pH of in the range of about 10 and 13, preferably between about 11 and 12. Any of the bases described herein as being suitable for use in the denaturation solution may also be used in the hybridization buffer. In addition, the hybridization buffer may further include about 20-60% formamide and about 5-40% dextran sulfate. In one embodiment, the hybridization buffer contains about 30-50% formamide, about 10% dextran sulfate and about 1-3 mM NaOH, and has a pH in the range of about 11 to about 12. In another embodiment, the hybridization buffer contains about 4.2 mM NaOH, about 42% formamide and about 28% dextran sulfate.

In yet another embodiment, the hybridization buffer comprises formamide and one or more salts (e.g., sodium salts) at a final concentration of about 0.03M to about 0.09M instead of a base. Preferably, the one or more salts include sodium citrate. Other suitable salts for use in the hybridization buffer include sodium chloride.

The kits of the invention further include one or more wash buffers. In a particular embodiment, the one or more wash buffers each comprise one or more bases (e.g., NaOH) and have a pH of between about 10 and 13, preferably between about 11 and 12. Any of the bases described herein as being suitable for use in the denaturation and hybridization buffers may also be used in the wash buffer. Preferably, the one or more wash buffers include about 1x-5xSSC and about 1-10 mM base. In a particular embodiment, the wash buffer contains about 2xSSC and about 1.75 mM NaOH, and has a pH of about 11. In another embodiment, the wash buffer contains about 2xSSC and about 3 mM NaOH.

In yet another embodiment, the one or more wash buffers each comprise one or more salts (e.g., sodium salts, lithium salts or potassium salts) at a final concentration of about 0.03M to about 0.09M and no base. In a particular embodiment, the wash buffer includes sodium citrate and sodium chloride. The wash buffers may further comprise a detergent including, but not limited to, sodium dodecyl sulfate (SDS). Suitable concentrations of SDS in the wash buffers are typically in the range of about 0.01% to about 1.0% SDS, preferably about 0.1% SDS. In addition, the wash buffers in the kits of the invention may optionally include formamide.

Additional containers providing one or more reagent(s) for detecting the labeled probe can also be included in the kits of the invention. Such additional containers can include reagents or other elements recognized by the skilled artisan for use in a detection assay corresponding to the type of label on the probe. In one embodiment, the probes in the kit comprise an indirect label (e.g., biotin) and the kit further includes at least a secondary agent for detecting the indirect label (e.g., a container providing streptavidin labeled with a fluorophore).

A description of example embodiments of the invention follows.

Example 1: A FISH Procedure Employing a Room Temperature Denaturation Step and Standard, Elevated Temperature Hybridization Step and Wash Cytogenetic Slide Preparation Human chromosome slides were prepared by harvesting peripheral blood cultures from an individual male donor. One mL peripheral blood per 25 mL culture flask from the donor was cultured in 10 mL RPMI 1640, 2 mM L-glutamine, FBS 10%, 250 µL PHA at 37° C. and 5% $CO_2$. After 72 hours of culture, the cells were arrested in mitosis by adding 0.6 µl of colcemid (Karyomax, Invitrogen) per mL of culture. After 20 min at 37° C., the cultures were centrifuged 10 min at 1750 rpm, the supernatant was discarded and 10 mL of hypotonic solution, and 75 mM KCl, was carefully added. After incubating for 20 min at 37° C., several drops of Carnoy's fixative (Methanol:acetic acid, 3:1) were added to the tubes in order to perform a prefixation of the cells and facilitate further fixation without cell clumping. After centrifugation, cells were re-suspended in Carnoy's fixative. The fixation step was repeated 3 times until the pellets were clearly white. During the last fixation, the correct amount of fixative required for slide preparation was determined. Spreading was done at ~22° C. and ~50% humidity on SuperFrost® slides with one or two drops of cell suspension per slide. The slides were kept overnight at 37° C. and then stored at −20° C. in hermetic boxes with a desiccant until FISH was performed.

Probes

X and Y Oligo-FISH® probes (Cellay, Inc., Cambridge, Mass.) were utilized. The probes were synthesized and labeled by Thermo Fisher Scientific (Ulm, Germany) using the DY fluors from Dyomics, GmbH (Jena, Germany). Chromosome X probe is labeled with the DY590 fluorescent dye and consists of 10 ODNs. The DXZ1 repeated 2 Kb sequence is present approximately 5,000 times in the pericentromeric region of human X chromosome (Yang 1982). This 2 Kb region consists of twelve 171-bp α-monomers arranged in imperfect direct repeats permitting X chromosome α-satellite repeat probes to be designed. To avoid cross hybridization to other chromosome α-satellite repeats, probes were designed to correspond to regions of the DXZ1 locus that have lower homology with the consensus α-monomer sequence. Chromosome Y probe consists of 4 ODNs and is labeled with the DY490 fluor. The DYZ1 region on Yq12 chromosome band consists of a 3.4 kb sequence element present in 500 to 3000 copies. Throughout this repeat, high copy number TTCCA satellite 3 pentamer sequence repeats are interspersed among unique Y-chromosome specific sequence elements of varying length (Nakahori 1986; Weier 1990; Nakagome 1991). Ideally, for optimal hybridization, synthetic ODN Y-probes will be underrepresented for the TTCCA pentamer and will consist primarily of sequences comprised of approximately 50% CG-bases. 30 mer ODN probes were designed for this region and compared to the human whole genome database (NCBI) using the Basic Local Alignment Tool (BLAST) (Altschul 1990). The sequences were compared to the non redundant genomic database (nr) with no filter.

FISH Employing Room Temperature Denaturation and Conventional Hybridization Steps Prepared cytogenetic slides harvested from human peripheral blood were denatured in a solution of NaOH in 70% ethanol at 21° C. for varying denaturation times ranging from 3 min. to 20 min. Different concentrations of NaOH ranging from 0.03 M to 0.17 M were tested. The slides were then dehydrated by an ethanol gradient (80%, 90%, and 100%) for 2 min each and air dried. Equal volumes of hybridization buffer and probe cocktail were mixed to obtain the hybridization mix used in this procedure. Cocktails were used in a working volume of 10 µL. The area of interest on each slide was located with a phase contrast microscope and a 10 µL volume of OligoFISH® X, Yq12 cocktail was dropped on the slide and covered with a 22 mm×22 mm coverslip. The hybridization was carried out at 37° C. for 5 min. After hybridization, the slides were washed in 2×SSC under agitation to remove the coverslip and then washed (0.2×SSC, 0.1% SDS) at 50° C. for 2 min with agitation for 30 sec. Finally, slides were collected in 2×SSC, mounted with antifade with DAPI and covered with a 50 mm×22 mm cover slip (#1 thickness). FISH data using the average signal-to-noise ratio (SNR) taken from 50 interphase nuclei for each probe were compared.

Determination of Signal Intensity

Signal intensity was determined by the signal-to-noise ratio (SNR). Using NIS-Elements software, FISH images from 50 interphase nuclei (minimal number required for statistical analysis), acquired under identical conditions, were segmented by the threshold value of the gray level to differentiate between signal and cell nucleus. For each cell, the gray level mean, defined as the sum of gray levels in the measured segment, divided by the segment area in pixels, and standard deviation were calculated. Signal to noise ratio was then determined as the signal mean gray level divided by the background mean gray level.

Fluorescence Microscopy and Image Acquisition

Fluorescence microscopy analysis and digital image capture were performed using a Nikon Eclipse 90i microscope (Nikon Instruments, Melville, N.Y.) equipped with a Cool-SNAP™ HQ2 CCD camera (Photometrics Ltd., Tucson, Ariz.). Images were captured and measured using Nikon NIS-Elements software.

Results

Of the different NaOH concentrations tested, 0.07 M NaOH in 70% ethanol gave the highest SNR. In addition, 10 min. was found to be the optimal denaturation time. FIG. 1 shows that room temperature denaturation for 10 min. produced statistically similar SNRs for X and Y probes compared to conventional denaturation (70% formamide at 72° C.), when conventional hybridization (37° C.) and wash (50° C.) temperatures were employed for both procedures.

Example 2: A FISH Procedure Employing Room Temperature Denaturation and Wash

FISH Employing Room Temperature Denaturation and Wash

Prepared cytogenetic slides harvested from human peripheral blood (described in Example 1) were denatured in 0.07 M NaOH in 70% ethanol at 21° C. for 15 min. The slides were then dehydrated by an ethanol gradient (80%, 90%, and 100%) for 2 min each and air dried. The area of interest on each slide was located with a phase contrast microscope and a 10 µL volume of OligoFISH® X, Yq12 cocktail was dropped on the slide and covered with a 22 mm×22 mm coverslip. The hybridization was carried out at room temperature (about 21° C.) for 10 min. After hybridization, the slides were washed in 2×SSC for 5 min. under agitation to remove the coverslip. After the hybridization, the slides were washed in 2×SSC buffers with various concentrations of NaOH (1, 2 and 3 mM) at room temperature for 5 minutes. Finally, slides were collected in 2×SSC, mounted with antifade with DAPI and covered with a 50 mm×22 mm cover slip (#1 thickness). FISH data using the average signal-to-noise ratio (SNR) taken from 50 interphase nuclei for each probe were compared. The 1 mM NaOH gave strong signals but some secondary signals were visible, the 2 mM gave weaker signals but very specific. So further concentrations of NaOH were tested, 1, 1.25, 1.50, 1.75 and 2 mM. The 1.75 mM NaOH 2×SSC at room temperature gave very similar results to the hot wash in 0.2×SSC 0.1% SDS at 48° C.

Cytogenetic slide preparation, probes, determination of signal intensity and fluorescence microscopy and image acquisition were performed as generally described in Example 1.

Results

Figure 2:
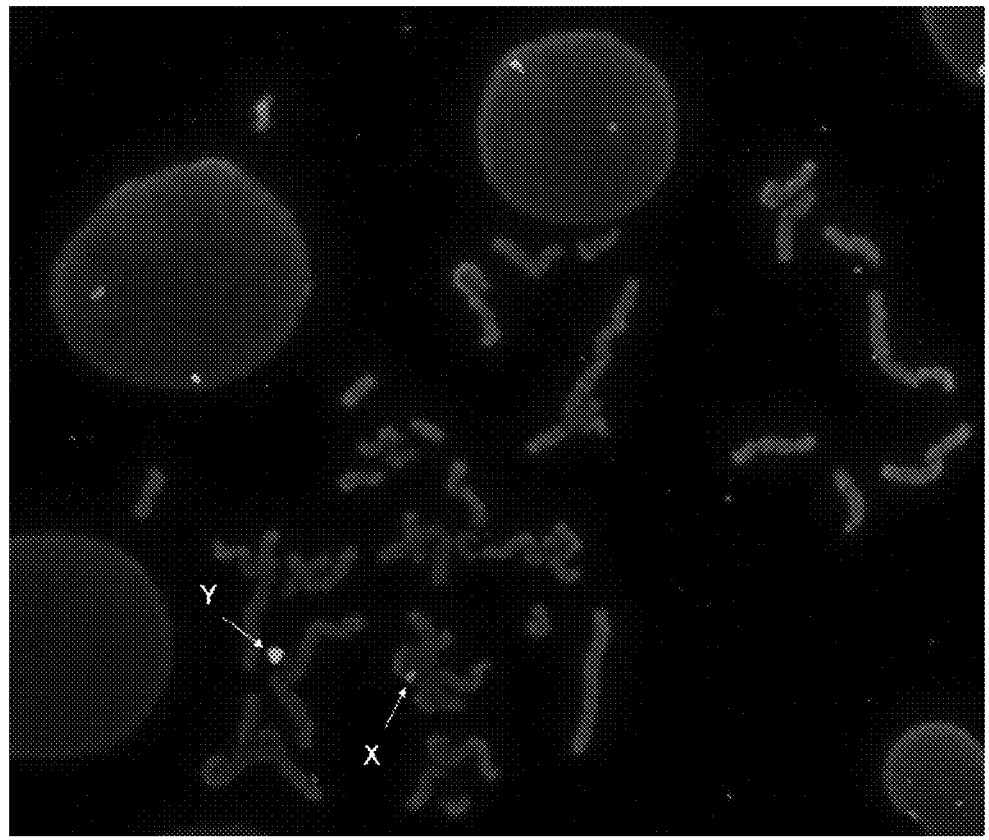
FIG. 2 is an image of a metaphase chromosome spread and interphase nuclei from peripheral blood showing signals produced by Oligo-FISH® X- (red) and Y-chromosome (green) (arrows) probes following FISH using room temperature denaturation and hybridization steps and standard wash conditions.

After establishing optimal conditions for room temperature denaturation, a room temperature wash condition (21° C. hybridization, 5 min.) was tested using the same hybridization buffer used for conventional FISH described in Example 1, combined with pre-treatment/denaturation in 0.07 M NaOH/70% ethanol for 10 min. at room temperature. The same OligoFISH® X and Y probe set and conventional wash conditions (0.2×SSC, 0.1% SDS, 50° C.) employed in Example 1 herein were used. Room temperature wash images are shown in FIG. 2. FISH signals for X (red) and Y (green) probes are clearly seen in interphase nuclei, as well as on the corresponding chromosomes in the metaphase spread.

Example 3: A FISH Procedure for Peripheral Blood Cells Employing a Hybridization Step Performed at Room Temperature and Under Basic Conditions Hybridization buffers with various concentrations of sodium hydroxide were prepared and tested in a FISH procedure using the room temperature denaturation step described in Example 1 and the room temperature wash described in Example 2. Slides that were subjected to the hot 70% formamide denaturation step and 50° C. wash were also included to show independence of the room temperature hybridization step over other room temperature treatments that included a probe hybridization step performed at room temperature (22.7° C.) for 5 minutes. The concentrations of NaOH in the hybridization buffers tested were 1, 2, 3 and 4 mM. The concentration of formamide and Dextran Sulfate were the same as in Example 1, but the 2×SSC was removed to avoid buffering the pH. The results obtained with each sodium hydroxide hybridization buffer under room temperature hybridization conditions (i.e., signal-to-noise ratios) were compared to results obtained when hybridization was carried out at 37° C. for 5 minutes with a standard hybridization buffer (2×SSC, 30% Formamide, 20% Dextran sulfate). For select buffers, a signal to noise analysis was performed as described in Example 1. All experiments were performed using untreated peripheral blood slides. A panel of OligoFISH® probes for the enumeration of chromosomes 3 (gold), 6 (aqua), 7 (green) and 20 (red) were used for all hybridizations.

Figure 3:
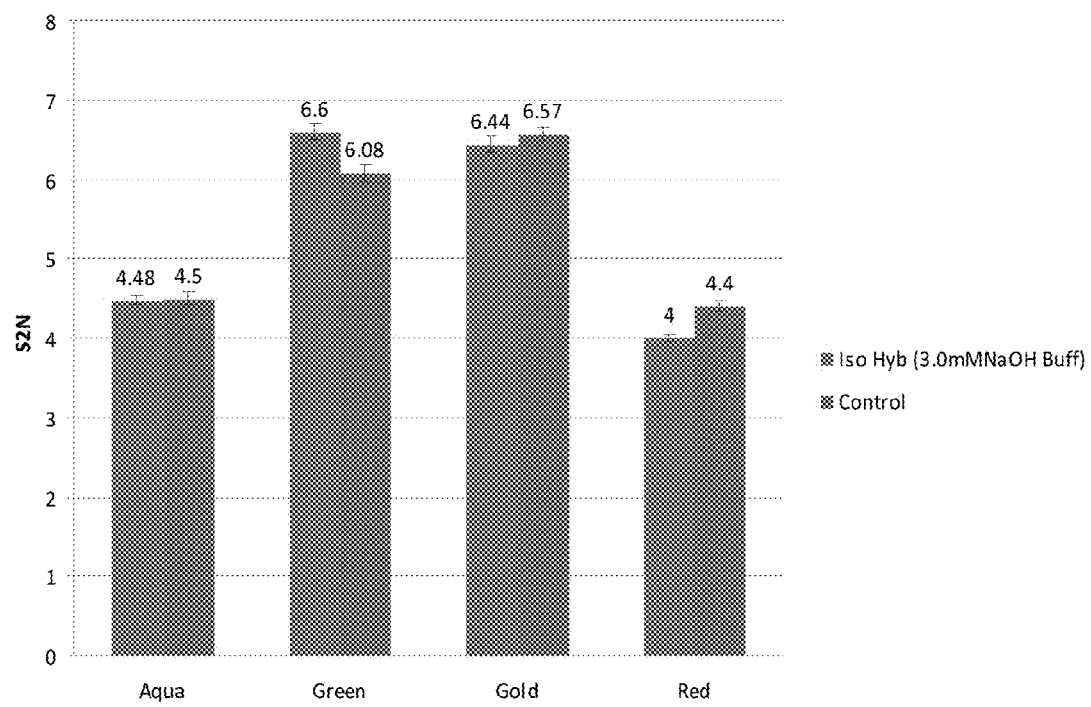
FIG. 3 is a graph depicting the signal-to-noise ratio for chromosome 3 (gold), chromosome 6 (aqua), chromosome 7 (green) and chromosome 20 (red) probes after hybridization at room temperature (Iso Hyb (3.0 mM NaOH Buff)) or at 37° C. (control) on untreated peripheral blood cells.

Room temperature hybridization with a hybridization buffer consisting of 3 mM NaOH, 30% formamide, and 20% dextran sulfate produced signals that were visually indistinguishable from those produced by hybridization with the standard buffer at 37° C. Signal-to-noise data obtained for peripheral blood slides using the 3 mM NaOH, 30% formamide, and 20% dextran sulfate hybridization buffer under room temperature conditions were also very similar to data obtained using the standard hybridization buffer (2×SSC, 30% formamide, 20% dextran sulfate) at 37° C. (FIG. 3).

Example 4: A FISH Procedure for Urothelial Cells Employing Pretreatment at Room Temperature Followed by Denaturation, Hybridization and Wash Steps all Performed at Room Temperature and Under Basic Conditions A FISH procedure employing room temperature protease treatment, denaturation, hybridization and wash steps was performed on urothelial slides. The protease treatment was performed with 0.2% pepsin for 15 minutes at room temperature, followed by a brief fixation in 1% formalin. Denaturation was performed in 0.07 M NaOH/70% ethanol for 10 min. at room temperature, followed by a dehydration in 85% and 100% ethanol for 1 minute each. Hybridization was performed with OligoFISH® probes for the enumeration of chromosomes 3, 6, 7 and 20 in 3 mM NaOH, 30% formamide, and 20% dextran sulfate hybridization buffer under room temperature conditions for 10 minutes. The wash of the slides was performed at room temperature for 5 minutes in 1.75 mM NaOH 2×SSC at room temperature. Results were compared to those obtained when protease, denaturation, hybridization and wash were performed at hot temperatures using standard reagents for FISH. For both sets of conditions, probes were hybridized to the samples for 10 minutes. Signal to noise analysis was performed as described in Example 1.

Figure 4:
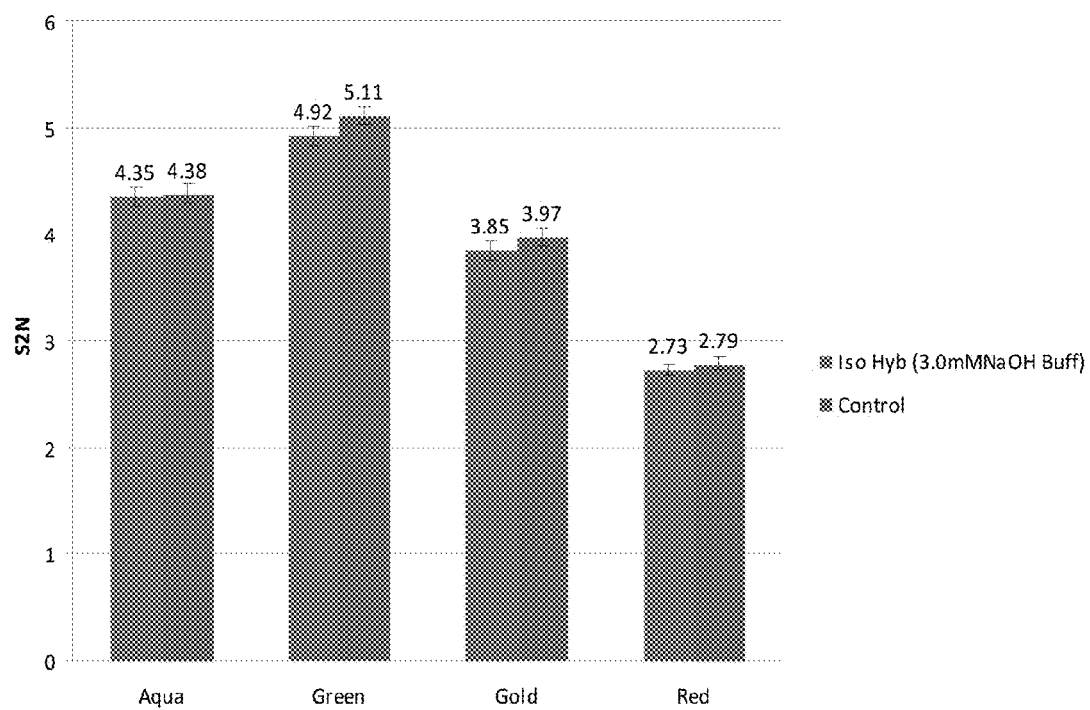
FIG. 4 is a graph depicting the signal-to-noise ratio for chromosome 3 (gold), chromosome 6 (aqua), chromosome 7 (green) and chromosome 20 (red) probes after hybridization at room temperature (Iso Hyb (3.0 mM NaOH Buff)) or at 37° C. (control) on urothelial cells.

The procedure employing all room temperature treatments yielded signals that were indistinguishable from those obtained by hybridization with the standard buffers at higher temperatures. Analysis of the signal to noise ratios (FIG. 4) generated by each procedure revealed concordant results. Thus, room-temperature conditions utilizing a higher concentration protease and an alkaline denaturation, hybridization and wash may be employed successfully on FISH procedures performed on urothelial cells.

Figure 5:
FIG. 5 is an image of a peripheral blood slide that has been hybridized at room temperature with a unique sequence chromosome 13 probe prepared from a BAC according to the FISH protocol described in Example 5 herein.

Example 5: A FISH Procedure for Peripheral Blood Cells Employing a Unique Sequence Probe Generated with BACs Using Denaturation, Hybridization and Wash at Room Temperature A FISH procedure involving a BAC probe located on chromosome 13 was performed successfully under several conditions (see, for example, FIG. 5). First the slides were denatured for 3 minutes in 70% formamide 2×SSC at 72° C. The BAC probe labeled in green was re-suspended in a hybridization buffer consisting of 42% Formamide, 28% Dextran and 2.8×SSC. The BAC was denatured in this mixture at 72° C. for 10 minutes and permitted to re-hybridize to the repetitive sequences at 37° C. for 30 minutes. The probe was applied to the slides and allowed to hybridize overnight at 37° C. Afterwards, the slides were washed at 72° C. for 5 minutes in 0.2×SSC 0.3% NP40. In order to test if the same room temperature denaturation used for the OligoFISH® probes would work, a peripheral blood slide was treated with 0.07 M NaOH in 70% ethanol for 10 minutes, and followed with the traditional protocol as described in Example 1 herein. The specificity and intensity of the probe signals were indistinguishable from the slide that had been denatured with hot formamide.

Next, a room temperature wash was performed for 5 minutes in 1.75 mM NaOH 2×SSC and the same results were obtained, yielding signals that were indistinguishable from the slide washed at 72° C. with 0.2×SSC 0.3% NP40. Finally, different concentrations of NaOH (2, 3, 4 and 5 mM) were tested in the hybridization buffer to determine the right conditions for the unique sequence probes to hybridize at room temperature. While maintaining the concentration of formamide at 42% and the Dextran sulfate at 28%, the 2×SSC was removed to avoid any buffering of the NaOH. The slides were hybridized at room temperature overnight. It was clear that 4 mM was giving quite similar, but slightly dimmer, signals compared to the slide hybridized at 37° C. Therefore, to optimize the concentration of NaOH in the hybridization buffer, concentrations of 4, 4.2, 4.4, 4.8 and 5 mM were tested on new slides. The buffer with 4.2 mM NaOH provided signals that were visually indistinguishable from the slide hybridized at 37° C. with the traditional hybridization buffer.

The relevant teachings of all patents, published applications and references cited herein are incorporated by reference in their entirety.

While this invention has been particularly shown and described with references to example embodiments thereof, it will be understood by those skilled in the art that various changes in form and details may be made therein without departing from the scope of the invention encompassed by the appended claims.

What is claimed is:

1. A method for detecting a target nucleic acid in a biological sample fixed on a solid support, wherein the target nucleic acid is DNA, the method comprising the steps of:
   a) hybridizing at least one DNA probe to the target nucleic acid in the sample fixed on the solid support at a temperature in the range of about 19 degrees Celsius to about 25 degrees Celsius, thereby forming a hybridization complex on the solid support comprising the at least one DNA probe and the target nucleic acid, wherein the probe:
   1) is present in a hybridization buffer comprising about 1-3 mM NaOH, about 20-60% formamide, and about 5-40% dextran sulfate and
   2) comprises a nucleotide sequence that is substantially complementary to a nucleotide sequence in the target nucleic acid and at least one detectable label;
   b) after step a), washing the solid support in a wash buffer comprising about 1-3 mM NaOH at a temperature in the range of about 19 degrees Celsius to about 25 degrees Celsius to remove the at least one DNA probe that has not hybridized to the target nucleic acid; and
   c) detecting the at least one detectable label on the at least one DNA probe of the hybridization complex on the solid support, thereby detecting the target nucleic acid in the sample fixed on the solid support.

2. The method of claim 1, wherein the hybridization buffer has a pH of about 11.

3. The method of claim 1, wherein the duration of step a) is about 5 minutes to about 15 minutes.

4. The method of claim 1, wherein the probe is a single-stranded oligonucleotide probe comprising about 20 to about 50 nucleotides.

5. The method of claim 1, wherein the probe is prepared from a genomic fragment.

6. A method for detecting a target nucleic acid in a biological sample fixed on a solid support, wherein the target nucleic acid is DNA, the method comprising the steps of:
   a) denaturing a biological sample fixed on a solid support, wherein the sample comprises the target nucleic acid, in a denaturation buffer comprising about 0.03 N to about 0.17 N base and about 50% to about 90% alcohol by volume;
   b) hybridizing at least one DNA probe to the target nucleic acid in the sample fixed on the solid support, thereby forming a hybridization complex comprising the at least one DNA probe and the target nucleic acid on the solid support, wherein the probe comprises a nucleotide sequence that is substantially complementary to a nucleotide sequence in the target nucleic acid and at least one detectable label and is present in a hybridization buffer that comprises about 1-3 mM base;
   c) after step b), washing the solid support in a wash buffer having a pH of about 10 to about 11, the wash buffer comprising about 1-3 mM base; and
   d) detecting the at least one detectable label on the at least one DNA probe of the hybridization complex on the solid support, thereby detecting the target nucleic acid in the sample fixed on the solid support,
      wherein each of steps a), b) and c) is performed at a temperature in the range of about 19 degrees Celsius to about 25 degrees Celsius.

7. The method of claim 6, wherein the wash buffer has a pH of about 11.

8. The method of claim 7, wherein the base in the wash buffer is NaOH and the wash buffer further comprises about 2×SSC.

9. The method of claim 6, wherein the base in the denaturation buffer, hybridization buffer and wash buffer is NaOH.

10. A method for determining whether a target nucleic acid is present in a biological sample fixed on a solid support, wherein the target nucleic acid is DNA, the method comprising the steps of:
    a) denaturing a biological sample fixed on a solid support in a denaturation buffer comprising about 0.03 N to about 0.17 N base and about 50% to about 90% alcohol by volume;
    b) incubating at least one DNA probe with the sample fixed on the solid support, thereby forming a hybridization complex comprising the at least one DNA probe and the target nucleic acid on the solid support when the target nucleic acid is present in the sample, wherein the probe comprises a nucleotide sequence that is substantially complementary to a nucleotide sequence in the target nucleic acid and at least one detectable label and is present in a hybridization buffer that comprises about 1-3 mM base;
    c) after step b), washing the solid support in a wash buffer comprising about 1-3 mM base; and
    d) determining whether the target nucleic acid is present in the sample fixed on the solid support by detecting the hybridization complex on the solid support;
    wherein each of steps a), b) and c) is performed at a temperature in the range of about 19 degrees Celsius to about 25 degrees Celsius.

\* \* \* \* \*